United States Patent [19]

Miraldi

[11] 4,158,040
[45] Jun. 12, 1979

[54] RAPID STERILIZATION EVALUATOR AND TEST APPARATUS

[75] Inventor: Peter T. Miraldi, Erie, Pa.

[73] Assignee: American Sterilizer Company, Erie, Pa.

[21] Appl. No.: 888,571

[22] Filed: Mar. 20, 1978

[51] Int. Cl.² .......................... A61L 3/02; B01J 3/04; G01N 1/02

[52] U.S. Cl. ..................... 422/297; 73/425.2; 73/432 SD

[58] Field of Search ............... 21/56, 91–98, 21/103, 104; 23/290; 73/425.2, 432 SD

[56] References Cited
U.S. PATENT DOCUMENTS

| | | | |
|---|---|---|---|
| 2,244,082 | 6/1941 | Reyniers | 21/98 |
| 2,646,268 | 7/1953 | Jackson | 21/93 |
| 3,147,068 | 9/1964 | Castle et al. | 21/98 |

*Primary Examiner*—Sidney Marantz
*Assistant Examiner*—Bradley Garris
*Attorney, Agent, or Firm*—Charles L. Lovercheck

[57] ABSTRACT

A rapid sterilization evaluator and test apparatus having a media chamber and a work chamber. The media chamber is connected to the work chamber by a valve apparatus that can be opened from outside the media chamber when the work chamber is sealed so that the media conditions can be almost instantly established in the work chamber. Then, after a proper exposure period, the valve can be closed and the media chamber sealed off from the work chamber so that the work may be removed from the work chamber.

11 Claims, 4 Drawing Figures

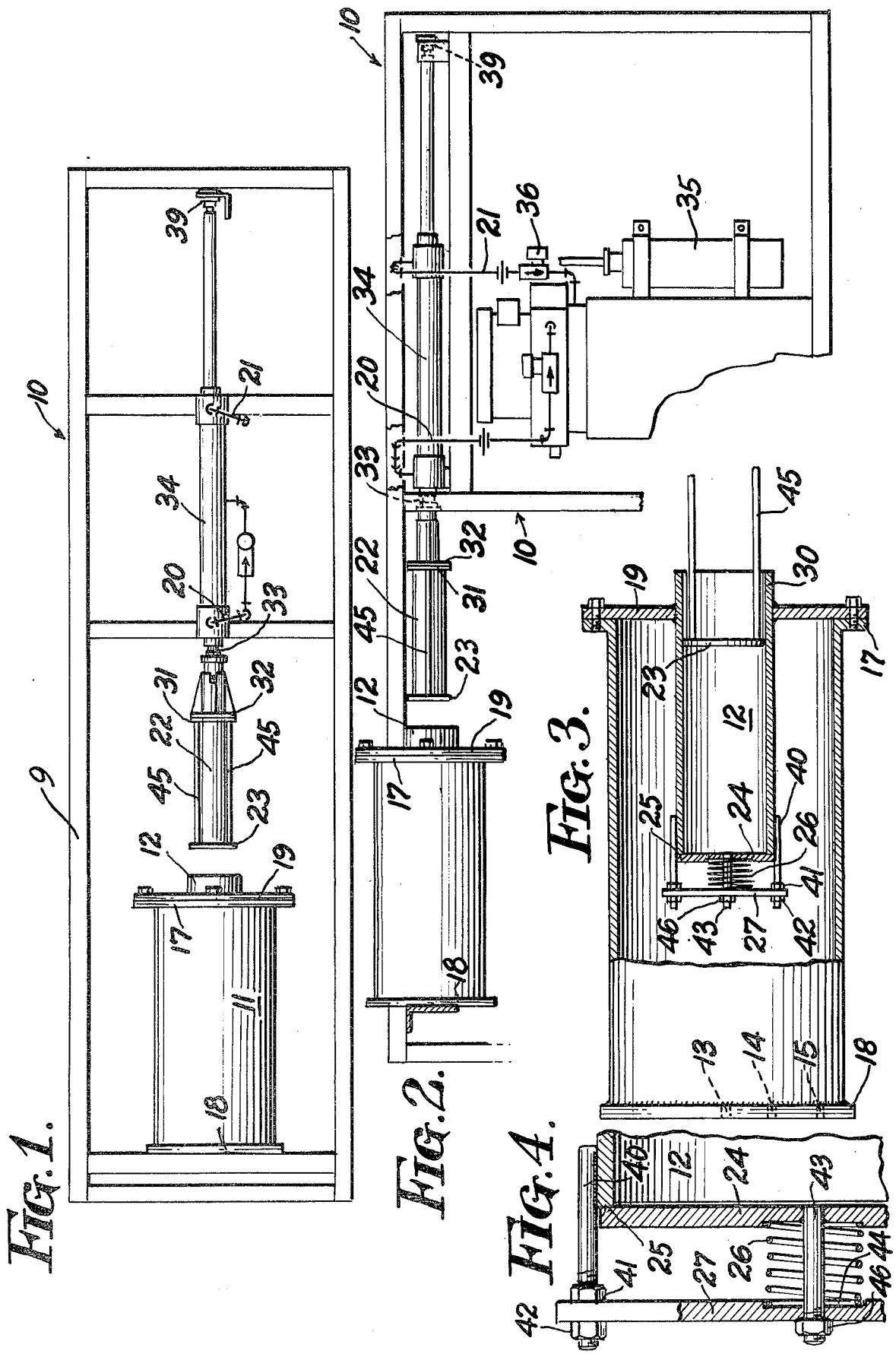

RAPID STERILIZATION EVALUATOR AND TEST APPARATUS

REFERENCE TO PRIOR ART

Applicant knows of no significant prior art. However, the U.S. Pat. No. 3,147,068 and U.S. Pat. No. 3,246,947 indicate the state of the art in the sterilizing field.

GENERAL STATEMENT OF THE INVENTION

A large chamber is provided, which may be sealed to contain a sterilizing media, such as saturated steam at the desired conditions of pressure and temperature, for example. The relatively small work chamber extends through one wall of the media chamber and has a closure or valve inside the media chamber similar to a check valve. A piston is slidably supported in the small work chamber. The piston may be supported from outside the chamber by means of a suitable hydraulic cylinder. When an article is supported on the piston, for example, and inserted in the small work chamber, a projection on the piston rod engages the check valve closure and opens it so that the steam in the media chamber immediately rushes into the small work chamber, thereby creating the same conditions of environment in the work chamber as prevails in the media chamber.

OBJECTS OF THE INVENTION

It is an object of the invention to provide an improved rapid steriliztion and test apparatus.

Another object of the invention is to provide in combination, a large chamber and a small chamber connected to the large chamber with a seal between them, which can be opened and closed from outside the sterilizer, thereby allowing the environment in the large chamber to be quickly established in the small chamber.

Another object of the invention is to provide a large cylindrical sealed chamber with a small chamber extending in to the large chamber through the walls of the large chamber with a piston movable in the small chamber and controlled from outside the chambers for opening a check valve between the two chambers, thereby allowing the rapid establishment of an atmospheric condition in the small chamber similar to the atmosphere in the large chamber.

Another object of the invention is to provide a rapid sterilization evaluator and test apparatus that is simple in construction, economical to manufacture and simple and efficient to use.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

GENERAL DESCRIPTION OF THE DRAWINGS

FIG. 1 is a top view of the rapid sterilization evaluator and test apparatus, according to the invention.

FIG. 2 is a side view partly broken away.

FIG. 3 is an enlarged partial view partly in section of the load media chamber and work chamber.

FIG. 4 is a enlarged partial view partly in section of the inner end of the work chamber.

DETAILED DESCRIPTION OF THE DRAWINGS

Now, with more particular reference to the drawing, the rapid sterilization evaluator and test apparatus is indicated generally at 10 and is made up principally of a media chamber 11 and a work chamber 12. The media chamber is supported on frame 9. The work chamber 12 extends through an opening in the door 19 of the media chamber and may be suitably welded thereto. The media chamber has openings 13, 14 and 15 to which a suitable supply of steam and vacuum may be connected to establish the desired conditions inside the media chamber. A drain opening may be provided at the bottom of the chamber, which may be connected to either a source of vacuum or to a drain line, depending on the judgment of the individual designer.

The door 19 is supported on the end 17 of the media chamber, and the end 18 is covered by a closure suitably welded in place or, otherwise, supported thereon.

The chamber 11 may be constructed of a suitable material such as stainless steel, or the like, and may be provided with a proper insulation or steam jacket, depending on the desires of the designer.

The small work chamber 12 will be substantially smaller in volume than the volume of the large media chamber. For example, the small chamber could have a volume of approximately one-fourth the volume of the large chamber 11, or the proportions could, otherwise be determined, depending upon the particular desires of the individual designer.

The work cylinder 12 is provided with a closure or cylinder head 24 on its inner end, which may be held in place against its o-ring seal 25 by a suitable compression spring 26. The spring plate 27 is supported on the rods 40 by suitable nuts 41,42 and the spring 26 is supported on the spring plate 27 and it urges the cylinder head 24 into sealing engagement with the o-ring seal 25.

The outer end 30 of the load cylinder 12 is open, and it slidably receives the piston 31, which has a suitable piston ring 32 around its outer periphery. The piston 31 is supported on the piston rod 33, which is carried by a suitable cylinder 34. The piston rod 33 has rods 45 fixed to it and rods 45 extend from the piston 31 and terminates at end member 23, and end member 23 will engage the cylinder head 24 when the piston rod is pushed to the extreme left position, thereby compressing spring 26 and allowing the gas or steam in the chamber 11 to rush into the cylinder 12, thereby subjecting the article supported in article support 22 to the conditions that prevail in the cylinder 12.

Cylinder 34 is supported on frame 9 at 39. It is a two-way cylinder actuated by control lines 20 and 21 on frame 9 to advance the article into the chamber or retract it.

The configuration of the cylinder 11 and the cylinder 12 could be changed to suit the taste of the individual designer. For example, the small cylinder 12 could be supported entirely outside of the large cylinder 11, so long as the interior of the two cylinders were connected together.

The relative volumes of chambers 11 and 12 can also vary within wide limits. The hydraulic system 35 made up of valve 36, a cylinder head assembly, and cylinder 34 are supported on frame 9 with suitable piping for introducing and withdrawing piston 31 into cylinder 12.

Piston 31 has a suitable o-ring 32 that seals inside cylinder 12.

The spring plate 27 is supported on rods 40 which are welded to cylinder 12 and the preload on head 24 can be adjusted by moving the plate 27 toward or away from head 24 by nuts 41 and 42. The head 24 is fixed to bolt 43 and the end 44 of bolt 43 slides in a hole in plate 27, and bolt 43 has nut 46 on its end which limits the movement of bolt 43 when the plate 27 is removed from bolts 40.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. A rapid sterilization evaluator and test apparatus comprising,
    a media chamber 11 and a work chamber 12,
    said media chamber 11 comprising,
    a sealed chamber having an opening in one side thereof receiving an end of said work chamber,
    check valve means 24 connecting said work chamber with said media chamber,
    a piston in said work chamber 12,
    means on said piston for supporting an article to be sterilized,
    and means on said piston extending beyond said article support means for operating said check valve when said piston is pushed into said work chamber thereby allowing atmospheric conditions in said media chamber to enter said work chamber.

2. The apparatus recited in claim 1 wherein said piston is supported on the piston rod of a hydraulic cylinder.

3. The apparatus recited in claim 1 wherein said work chamber is disposed generally concentric to said media chamber and extends there into a substantial distance.

4. The combination recited in claim 3 wherein said work chamber has a plurality of inlets connected thereto for introducing a suitable media and for controlling the pressure of said media.

5. The combination recited in claim 4 wherein said check valve means comprises,
    a cylinder head overlying an end of said work chamber and a seal disposed between said cylinder head and said end of said work chamber,
    a helical spring,
    a spring support carried by said work chamber and said spring supported on said spring support and engaging said cylinder head thereby urging said cylinder head to engagement with said seal on said work chamber.

6. A rapid sterilization evaluator and test apparatus comprising in combination a large cylinder and a small cylinder,
    a frame, said large cylinder having two ends with closure means on each of said two ends,
    said large cylinder supported on said frame, the small cylinder extending through one of said closure means into said large cylinder and having one end disposed outside said large cylinder,
    check valve means closing the other end of said small cylinder inside said large cylinder,
    a first piston adapted to be slidably received in said small cylinder, forming a seal with the walls of said small cylinder, a hydraulic cylinder supported on said frame,
    said hydraulic cylinder having a second piston therein and a piston rod extending therefrom,
    means on said piston rod for supporting an article to be tested,
    means on said first piston adapted to engage said check valve means when said first piston is moved into said small cylinder by said hydraulic cylinder,
    whereby said check valve is opened allowing the space in said large cylinder to communicate with the space in said small cylinder,
    whereby gas under pressure in said large cylinder can rush into said small cylinder thereby establishing the same conditions of temperature and pressure in said small cylinder and said large cylinder.

7. The combination recited in claim 6 wherein said check valve comprises rods attached to said small cylinder,
    a spring plate attached to said rods, said check valve comprises a cylinder head closing the end of said small cylinder in said large cylinder and a compression spring supported on said spring plate urging said cylinder head into closed sealing position with the end of said small cylinder in said large cylinder.

8. The combination recited in claim 7 wherein said cylinder head has a sealing ring thereon adapted to form sealing engagement between said cylinder head and said end of said small cylinder in said large cylinder.

9. The combination recited in claim 8 wherein said means on said first piston engaging said check valve comprises spaced rods extending from said first piston and adapted to engage said cylinder head when said first piston moves into said small cylinder forming a closure for said small cylinder and forcing said cylinder head away from said small cylinder.

10. The combination recited in claim 9 wherein means are provided on said small cylinder for supporting an article to be tested.

11. The combination recited in claim 9 wherein said first piston, said small cylinder and said rods for engaging said cylinder head are disposed relative to each other such that said first piston closes the end of said small cylinder remote from said large cylinder before said rods engage said cylinder head.

* * * * *